(12) United States Patent
Hudak

(10) Patent No.: US 6,926,526 B2
(45) Date of Patent: Aug. 9, 2005

(54) ENDODONTIC ADAPTER FOR A SONIC SCALER

(76) Inventor: Kenneth G. Hudak, 748 Elm St., Akron, OH (US) 44310

( * ) Notice: Subject to any disclaimer, the term of this patent is extended or adjusted under 35 U.S.C. 154(b) by 59 days.

(21) Appl. No.: 10/155,313

(22) Filed: May 24, 2002

(65) Prior Publication Data

US 2003/0219697 A1 Nov. 27, 2003

(51) Int. Cl.⁷ ................................................. A61C 1/07
(52) U.S. Cl. ........................ 433/102; 433/119; 433/124
(58) Field of Search ........................... 433/81, 86, 102, 433/118, 119, 127, 224, 124

(56) References Cited

U.S. PATENT DOCUMENTS

| | | | |
|---|---|---|---|
| 3,645,255 A | * | 2/1972 | Robinson ........................ 601/2 |
| 4,229,168 A | | 10/1980 | Scholz, Jr. |
| RE30,536 E | | 3/1981 | Perdreaux, Jr. |
| 4,295,827 A | | 10/1981 | Martin et al. |
| 4,330,278 A | * | 5/1982 | Martin ........................ 433/81 |
| 4,332,558 A | * | 6/1982 | Lustig ........................ 433/86 |
| 4,370,131 A | * | 1/1983 | Banko ........................ 433/86 |
| 4,417,578 A | * | 11/1983 | Banko ........................ 606/169 |
| 4,484,891 A | | 11/1984 | Nash |
| 4,571,183 A | | 2/1986 | Nash |
| 4,818,229 A | | 4/1989 | Vasile |
| 4,850,867 A | | 7/1989 | Senia et al. |
| 4,992,048 A | | 2/1991 | Goof |
| 5,040,978 A | * | 8/1991 | Falcon et al. ............... 433/125 |
| 5,236,358 A | | 8/1993 | Sieffert |
| 5,419,703 A | | 5/1995 | Warrin et al. |
| 5,927,977 A | | 7/1999 | Sale et al. |
| 6,186,422 B1 | * | 2/2001 | Hubner et al. ............... 239/589 |
| 6,257,887 B1 | * | 7/2001 | Heckerman et al. ........ 433/141 |
| 6,302,693 B1 | * | 10/2001 | Mena ......................... 433/172 |
| 6,312,255 B1 | | 11/2001 | Hudak |

* cited by examiner

Primary Examiner—Ralph A. Lewis
(74) Attorney, Agent, or Firm—Brouse McDowell; Roger D. Emerson; Heather M. Barnes

(57) ABSTRACT

The invention is an improved endodontic adapter for a sonic scaler consisting of a talon having a threaded end for insertion into the handle of the sonic scaler. A pair of downwardly pointed barbs protrudes radially from the side of the adapter for receiving an elastic ligature, which firmly holds the dental instrument such as file to the talon. The opposite end of the talon has a tapered shaft that receives an aperture drilled into the side of the dental instrument. The ligature is simply wrapped around the dental instrument on opposite sides of the talon and then the ends are wrapped around the downwardly pointing barbs.

14 Claims, 7 Drawing Sheets

ENDODONTIC ADAPTER FOR A SONIC SCALER

I. BACKGROUND OF THE INVENTION

A. Field of the Invention

The present invention relates generally to dental instruments and, more particularly, to an endodontic adapter with a novel means for attaching a sonic dental instrument to the handle of a sonic periodontal scaler.

B. Description of the Related Art

The daily brushing and flossing of one's teeth is one of the most important hygiene functions that people perform. Failure to do so will inevitably cause tooth decay and gum disease requiring frequent trips to the dentist and expensive repair work. Despite even the noblest of efforts cavities can still appear and require a visit to the dentist. As most people know, a trip to the dentist is a very frightening experience. The dentist's office is filled with a variety of strange looking devices and equipment. The most infamous device is the dental drill, which the dentist uses to drill out decayed tooth material from a tooth to make room for a filling. As most people will attest, this is a very unpleasant experience. Modem dentistry has yielded devices wherein the dental drill is mounted on the head of a sonic instrument. The vibrations of the sonic device are transmitted to the drill for removing decayed tooth material. A variety of other devices can also be mounted on the head of the sonic instrument such as files, reamers, broaches, spreaders, and pluggers each of which perform a different dental function. The present invention is an improved means and apparatus for attaching the dental instruments to the handle of the sonic scaler.

In the related art, there exist several patents for dental scalers and instruments attached to the scaler. Typically, these devices have a dental instrument attached to the head of the scaler. For instance, and of considerable relevance are U.S. Pat. Nos. 4,571,183 and 4,484,891 issued in the name of Nash, which discloses a vibratory endodontic scaler with a dental file attached to the head of the scaler via a thumbscrew. However, a problem with this method of attachment occurs because the vibrations from the vibratory means loosen the thumbscrew and the dental instrument becomes loose. This can be disastrous when the instrument is in the patient's mouth. The remainder of the prior art utilizes similar methods to attach the dental instruments to the head of the vibratory means.

Consequently, a need has been felt for providing an improved apparatus and method of attaching dental instruments and the like to the head of a sonic scaler. The development of the endodonic adapter for a sonic scaler fulfills this need.

II. SUMMARY OF THE INVENTION

The present invention comprises a mounting head and an elastic ligature operatively connected to the mounting head. The elastic ligature is adapted to secure a medical instrument to the mounting head. Briefly described according to one embodiment of the present invention, an improved endodontic adapter for a sonic scaler is provided consisting of a talon shaped mounting head having a threaded end for insertion into the handle of the sonic scaler. Located on the other end of the mounting head is a tapered shaft portion having a pair of downwardly pointed barbs, which protrude radially from the side of tapered shaft portion. The pair of barbs is for receiving an elastic ligature, which firmly holds a dental instrument such as an endodontic dental file to the adapter. The dental instruments used with the adapter have a specially formed aperture drilled radially into it so that the dental instrument may be placed onto the tapered shaft portion. To secure the dental instrument to the adapter, the elastic ligature is simply wrapped around the dental instrument on opposite sides of the tapered shaft portion and then the ends of the elastic ligature are wrapped around the downwardly pointing pair of barbs. The dental instrument is now securely attached to the tapered shaft portion of the adapter.

Accordingly, it is an object of the present invention to provide an improved adapter for holding a variety of dental instruments for a sonic scaler.

Another object of the present invention is to provide an apparatus, wherein the mounting head comprises a shaft having a first end and a second end and at least one barb extending from the shaft.

Still, another object of the present invention is to provide an apparatus, wherein the first end of the shaft is threaded.

Further, another object of the present invention is to provide an apparatus, wherein the second end of the shaft is tapered.

Still yet, another object of the present invention is to provide an apparatus, wherein the barb is arcuate.

Yet, another object of the present invention is to provide an apparatus, wherein the barb emanates from the shaft radially in a downwardly direction.

Another object of the present invention is to provide an apparatus, wherein the mounting head is talon shaped.

Still, another object of the present invention is to provide an apparatus, wherein the elastic ligature comprises a first end and a second end, the first and second ends of the elastic ligature adapted to engage the barb, wherein the elastic ligature is placed in tension when securing the medical instrument and the barb.

Further, another object of the present invention is to provide an apparatus, wherein the elastic ligature is positioned behind the shaft.

Yet, another object of the present invention is to provide an apparatus, wherein the mounting head is steel.

Still yet, another object of the present invention is to provide an apparatus, wherein the mounting head is plastic.

Another object of the present invention is to provide an apparatus, wherein the threaded end of the shaft threadably connects to a handle, wherein the threaded end is secured with an o-ring.

It is yet another object of the present invention is to provide a mounting head having a shaft with a first end and a second end; and, at least one barb extending from the shaft, the barb having opposing ends distally located from the shaft, the ends of the barb adapted to receive an associated elastic ligature.

Yet, another object of the present invention is to provide a mounting head, wherein the shaft and the barb support an endodontic dental instrument.

Still, another object of the present invention is to provide a mounting head, wherein an elastic ligature secures an instrument to the mounting head.

Further, another object of the present invention is to provide a mounting head, wherein the first end is threaded.

It is yet another object of the present invention is to provide a mounting head, wherein the second end is tapered.

Another object of the present invention is to provide a mounting head wherein the barb is integrally formed with the shaft.

Further, another object of the present invention is to provide a mounting head, further comprising an o-ring positioned on the first end of the shaft.

It is yet another object of the present invention to provide an endodontic dental instrument, comprising:

a mounting head, the mounting head having a first end and a second end, the mounting head having a threaded shaft at the first end for insertion into a handle of a sonic scaler, the second end having a tapered shaft portion;

an annular neck, the annular neck separating the threaded shaft from the tapered shaft portion;

a pair barbs, the pair of barbs pointing downwardly and emanating radially from opposite sides of the tapered shaft;

an endodontic dental instrument having an aperture defined therein for placing the dental instrument onto the tapered shaft of the mounting head; and, an elastic ligature having two ends, wherein the elastic ligature is adapted to secure the dental instrument to the tapered shaft portion by wrapping the elastic ligature around the dental instrument on opposite sides of the tapered shaft and wrapping the ends of the elastic ligature around the pair of barbs.

Still, another object of the present invention is to provide a method for securing a medical instrument to a mounting head of a medical device, the method comprising the steps of:

providing an elastic ligature having a first end and a second end, the mounting head having a shaft with a first and second end, the mounting head further comprising a pair of barbs extending from the shaft; the medical instrument having an aperture defined therein;

inserting the second end of the shaft into the aperture of the medical instrument; and, securing the dental instrument to the mounting head with the elastic ligature.

Yet, another object of the present invention is to provide a mounting head, wherein securing the dental instrument to the mounting head with the elastic ligature comprises the steps of:

wrapping the elastic ligature around the medical instrument; and, engaging the first and second ends of the elastic ligature to ends of the barbs, the elastic ligature being positioned behind the shaft, such that the elastic ligature is in tension.

Another object of the present invention is to provide a method for securing the dental instrument to the mounting head, further comprising the step of connecting the mounting head to a handle of the medical device.

It is yet another object of the present invention is to provide a method for securing the dental instrument to the mounting head, wherein the first end of the handle is threaded, the method further comprising the step of:

placing an o-ring over the threaded end of the handle; and, securing the mounting head to the handle.

It is another object of the present invention to provide an improved means for attaching a dental instrument to the head of a sonic scaler.

It is yet another object of the present invention to provide a means for attaching a dental instrument to the head of a sonic scaler that will not loosen from the vibrations of the sonic scaler.

Still other benefits and advantages of the invention will become apparent to those skilled in the art to which it pertains upon a reading and understanding of the following detailed specification.

III. BRIEF DESCRIPTION OF THE DRAWINGS

The invention may take physical form in certain parts and arrangement of parts, a preferred embodiment of which will be described in detail in this specification and illustrated in the accompanying drawings which form a part hereof and wherein.

IV. DESCRIPTION OF THE PREFERRED EMBODIMENT

Figure 1:
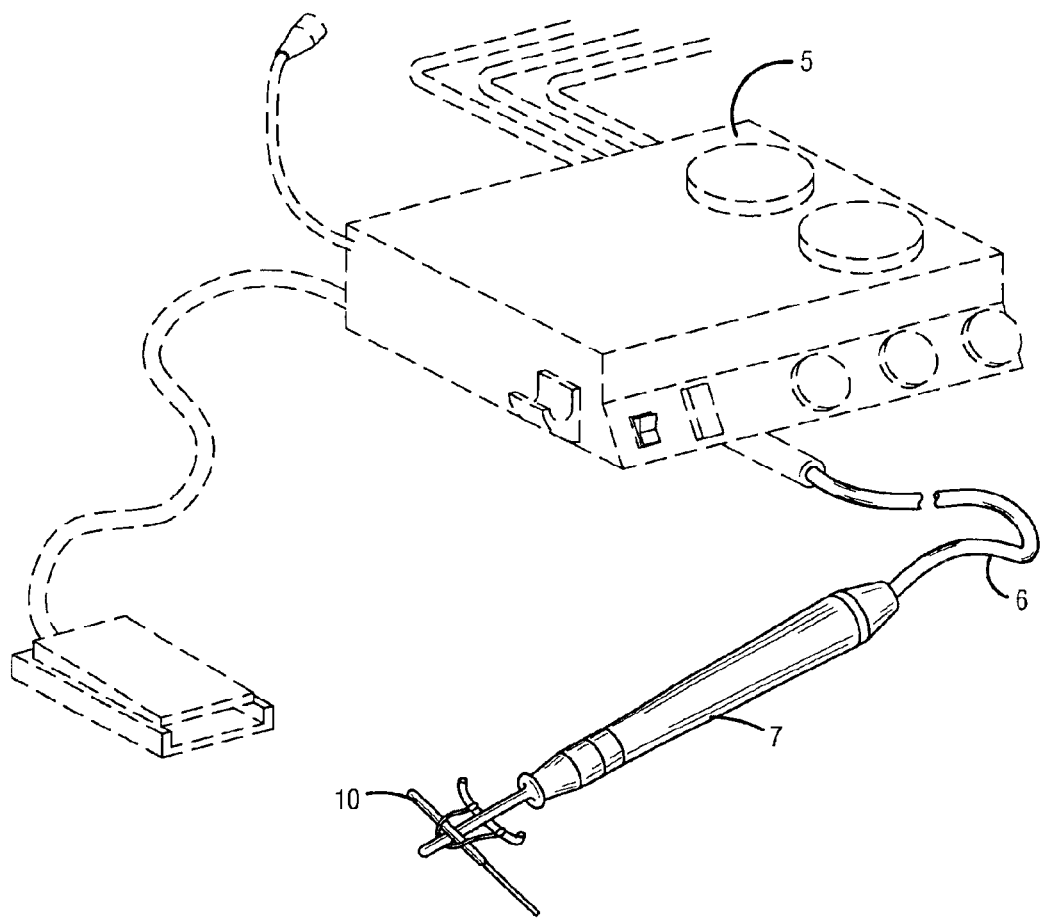
FIG. 1 is a perspective view of an endodonic adapter for a sonic scaler in the intended use, according to the preferred embodiment of the present invention.
Figure 2:
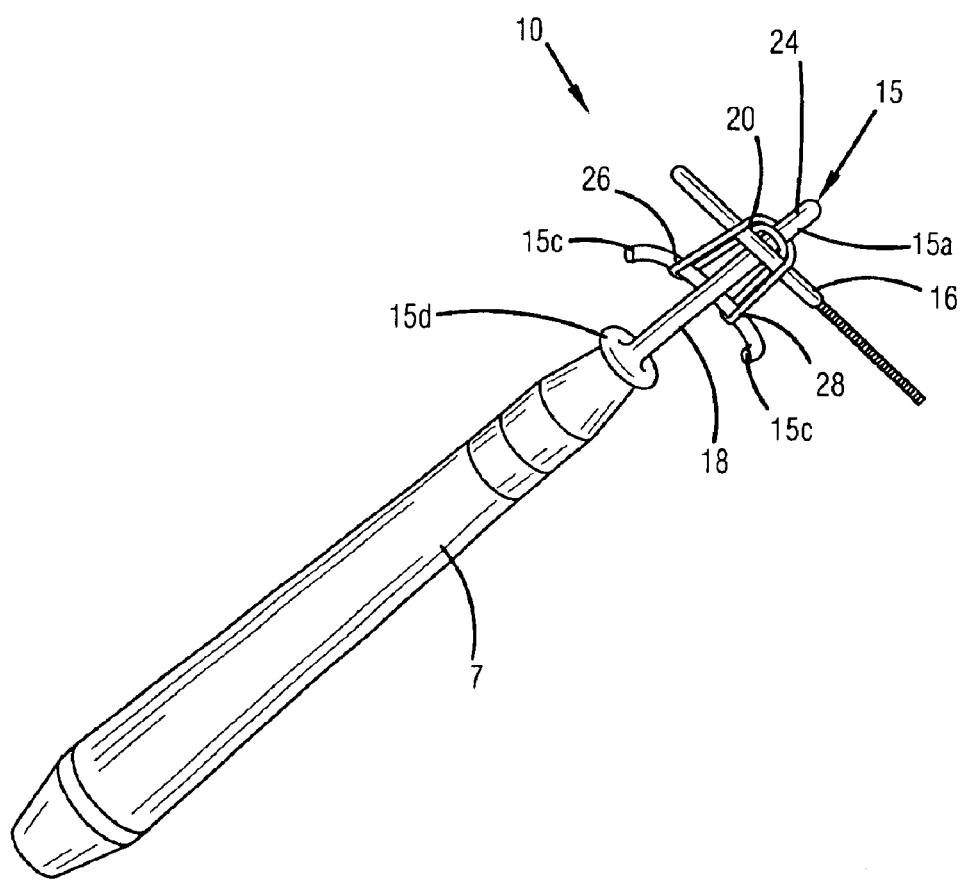
FIG. 2 is a perspective view of an endodonic adapter for a sonic scaler.

Referring now to the drawings wherein the showings are for purposes of illustrating a preferred embodiment of the invention only and not for purposes of limiting the same, FIGS. 1–6 illustrate the present invention. Referring now to FIGS. 1 and 2, an endodontic adapter 10 for a sonic scaler is shown, according to the present invention for attaching dental instruments to a handle 7 of a sonic scaler as shown in FIG. 2. Typically, most modern dental offices have a sonic scaler, best seen in FIG. 1, wherein an electrically powered base unit 5 generates sonic vibrations. The vibrations are transmitted by a tube 6 attached at one end to the base unit 5. The handle 7 is attached to the other end of the tube 6 for allowing the dentist to grip and manipulate the tube 6. Sonic scalers are well known in the art and will not be further described herein. A mounting head 15 is attached at the opposite end of the handle 7 wherein an assortment of dental instruments are attached for performing a variety of dental operations. The present invention is an improved mounting head 15 utilizing an elastic ligature 20 for securing the dental instrument 16 to the mounting head 15.

Figure 3:
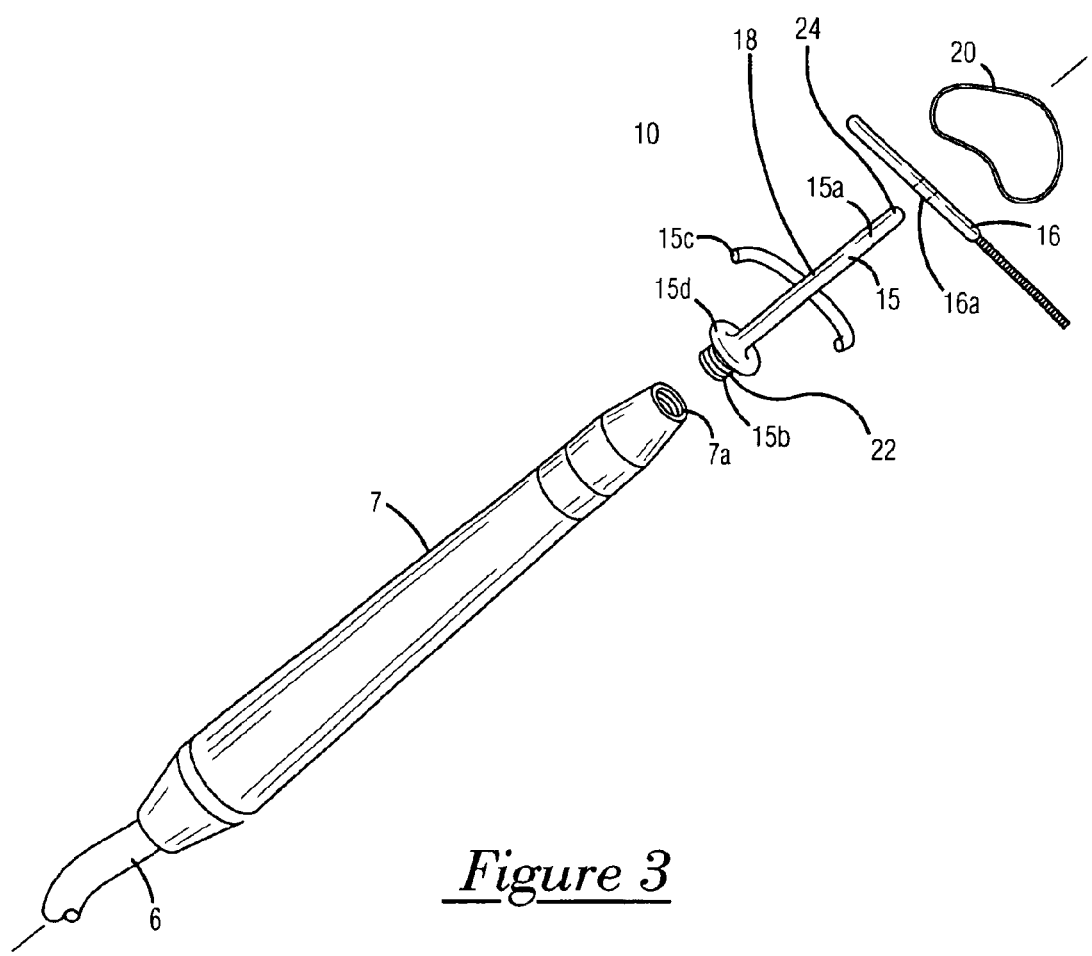
FIG. 3 is an exploded perspective view of an endodonic adapter for a sonic scaler, according to the preferred embodiment of the present invention.

With reference to FIGS. 1–5, the present invention comprises a mounting head 15 having a shaft 18 with a first end 22 and a second end 24 as shown in FIG. 3. The mounting head 15 may be talon shaped. What is meant by the term "talon shaped" is any configuration resembling a claw-like configuration. The first end 22 of the mounting head 15 may be threaded for insertion into the handle 7 of the sonic scaler, but any means for securing the mounting head 15 to the handle 7 may be utilized, which is chosen in accordance with sound engineering judgment. What is important is that the mounting head 15 is securely attached to the handle 7. When the first end 22 of the shaft 18 is threaded, the mounting head 15 is simply screwed into the threaded cavity 7a on the handle 7 of the sonic scaler 5. The second end 24 of the mounting head 15 has a shaft portion 15a that tapers to a point. It is also contemplated to be within the scope of the present invention that the second end 24 of the shaft 18 has a uniform cross section along its length.

Figure 4:
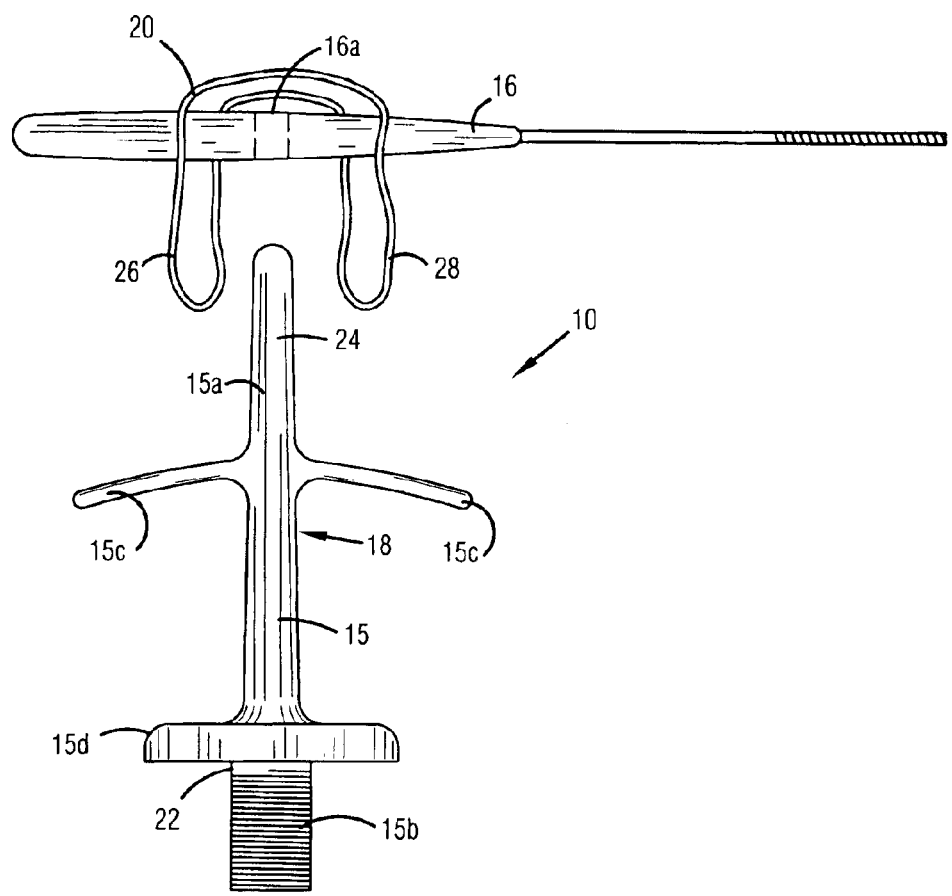
FIG. 4 is a front view of an endodonic adapter for a sonic scaler, according to the preferred embodiment of the present invention.
Figure 5:
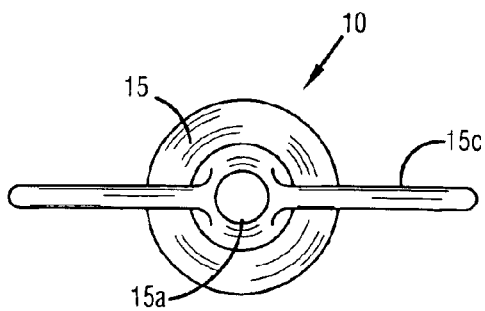
FIG. 5 is a top view of an endodonic adapter for a sonic scaler, according to the preferred embodiment of the present invention.

With reference to FIGS. 4 and 5, a pair of downwardly pointing barbs 15c emanate radially from opposite sides of tapered shaft portion 15a. Mounting head 15 and pair of barbs 15c are formed from a material such as stainless steel, rubber, or plastic but the materials are only meant as suggestions and in no way are limiting. An annular shaped neck 15d separates threaded shaft 15b and tapered shaft portion 15a. The pair of barbs 15c is arcuate in shape. As shown in FIGS. 4 and 5, the pair of barbs 15c is integrally formed with the shaft 18. However, it is also contemplated to be within the scope of the present invention for the mounting head to have one single barb securely attached to the shaft 18, such that the barb has opposing ends distally located from the shaft 18.

With continuing reference to FIGS. 4 and 5, the tapered shaft portion 15a is adapted to receive an aperture 16a drilled radially into any one of a number of common dental instruments such as drills, files, reamers, shapers, spreaders, and pluggers, hereinafter denoted as element 16 in the FIGURES. The dental instrument 16 is held securely to the tapered shaft portion 15a by a ligature 20 wrapped around the dental instrument 16 on opposite sides of shaft portion 15a. The ligature 20 should be at least partially elastic, and, as shown in the FIGURES, is fully elastic. What is meant by the term "elastic" is the capability of the ligature to return to about its original length or shape after being stretched. It should be understood that the ligature 20 may only be partially elastic in order to secure the dental instrument 16 to the mounting head 15. The ligature 20 has a first end 26 and a second end 28. The ends 26, 28 of ligature 20 are wrapped then secured around the pair of barbs 15c. The elastic ligature 20 is placed in tension when it secured the dental (or other medical instrument) to the pair of barbs 15c. The elastic ligature 20 is a typical ligature found in dental office and any ligature of roughly the right size can be used. Alternately, any type of elastic or rubber band may be substituted as long as suitable guarantees of sterility are observed.

To use the present invention depicted in FIGS. 1–5, an aperture 16a is drilled into the side of an endodontic dental instrument 16 such as a file, drill, reamer, broach, or plugger. The dental instrument 16 is inserted onto a specially formed shaft on an upper portion of the talon shaped mounting head. The dental instrument is held securely thereto by an elastic ligature wrapped around it on opposite sides of the shaft. The ligature is then secured by wrapping the ends of the ligature on a pair of downwardly pointing barbs protruding from opposite sides of the tapered shaft portion. The bottom portion of the mounting head has a threaded shaft portion for insertion into the handle of the endodonic sonic scaler. The base unit 5 is then turned on and the dental instrument inserted into the mouth of the patient. If another instrument is needed, it can quickly and easily be changed by pulling the elastic ligature from the barbs and removing the old dental instrument.

Figure 6:
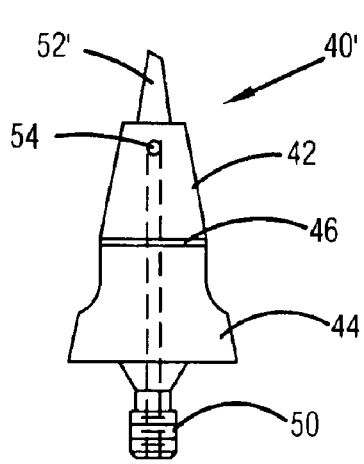
FIG. 6 is a side view of another embodiment of the present invention.
Figure 7:
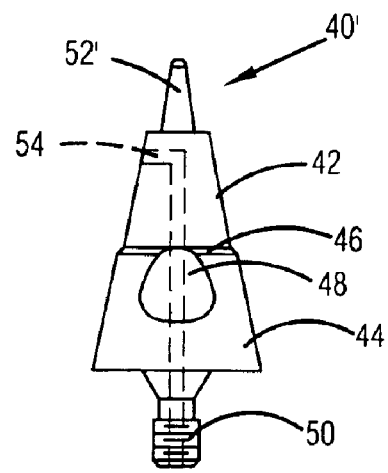
FIG. 7 is another side view of the present invention shown in FIG. 6.
Figure 8:
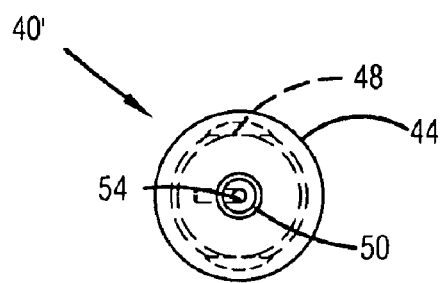
FIG. 8 is a bottom view of FIGS. 6 and 7.

With reference to FIGS. 6–10, another embodiment of the present invention is shown. A mounting head 40 is illustrated. The mounting head 40 comprises a first conical section 42 and a second conical section 44, which is interconnected by a shelf 46. The second conical section 44 comprises flat faces 48, which may aid in the attachment of the mounting head 40 to the handle 7 of the sonic unit 5. A first threaded shaft 50 extends from the second conical section 44. This threaded shaft 50 threads into the handle 7 of the sonic unit 5. It is not necessary that the shaft 50 be threaded. Any means may be utilized to secure the handle 7 to the sonic unit 5, which is chosen in accordance with sound engineering judgment. Further, a second threaded shaft 52 extends from the first conical section 42. The second threaded shaft 52 may be tapered with a chamfered edge as shown in FIGS. 6 and 7, or it may be uniform in cross-section as shown generally in FIGS. 9 and 10. The second threaded shaft 52 is adapted to be inserted into the aperture 16a of the dental instrument 16. The dental instrument 16 may have a handle portion formed from a rubber or polymeric material. Optionally, the elastic ligature 20 may take the form of an o-ring 30. The o-ring 30 may be inserted above the dental instrument 16 to secure the dental instrument 16 in place. The o-ring may be fabricated from rubber or any other polymeric material chosen with sound engineering judgment.

With continuing reference to FIGS. 6–10, the mounting head 40 may further comprise a water relief hole 54. The water relief hole 54 extends through the first and second conical sections 42, 44 and allows water to travel through the mounting head 15 during use. The threads on the first and second threaded shafts 50, 52 should be M3 threads or any other size thread chosen in accordance with sound engineering judgment. Further, the mounting head 40 may be manufactured from 303 stainless steel, a polymeric material, or any other material chosen in accordance with sound engineering judgment.

To use the present invention shown in FIGS. 6–10, an aperture 16a is drilled into the side of the endodontic dental instrument 16, such as a file, drill, reamer, broche, or a plugger. To insert the dental instrument 16 onto the second threaded shaft 52, the dental instrument 16 is rotated about the second threaded shaft 52. Even though the aperture 16a is not threaded itself, the threads of the second threaded shaft 52 provide for a tight friction fit. Friction between the dental instrument 16 and the second threaded shaft 52 holds the dental instrument 16 tightly in place. It should be understood that the aperture 16a may be threaded if desired. Optionally, the o-ring 30 may be inserted over the second threaded shaft 52 to further secure the dental instrument 16. The sonic unit 5 may then be used by the health care professional.

Figure 9:
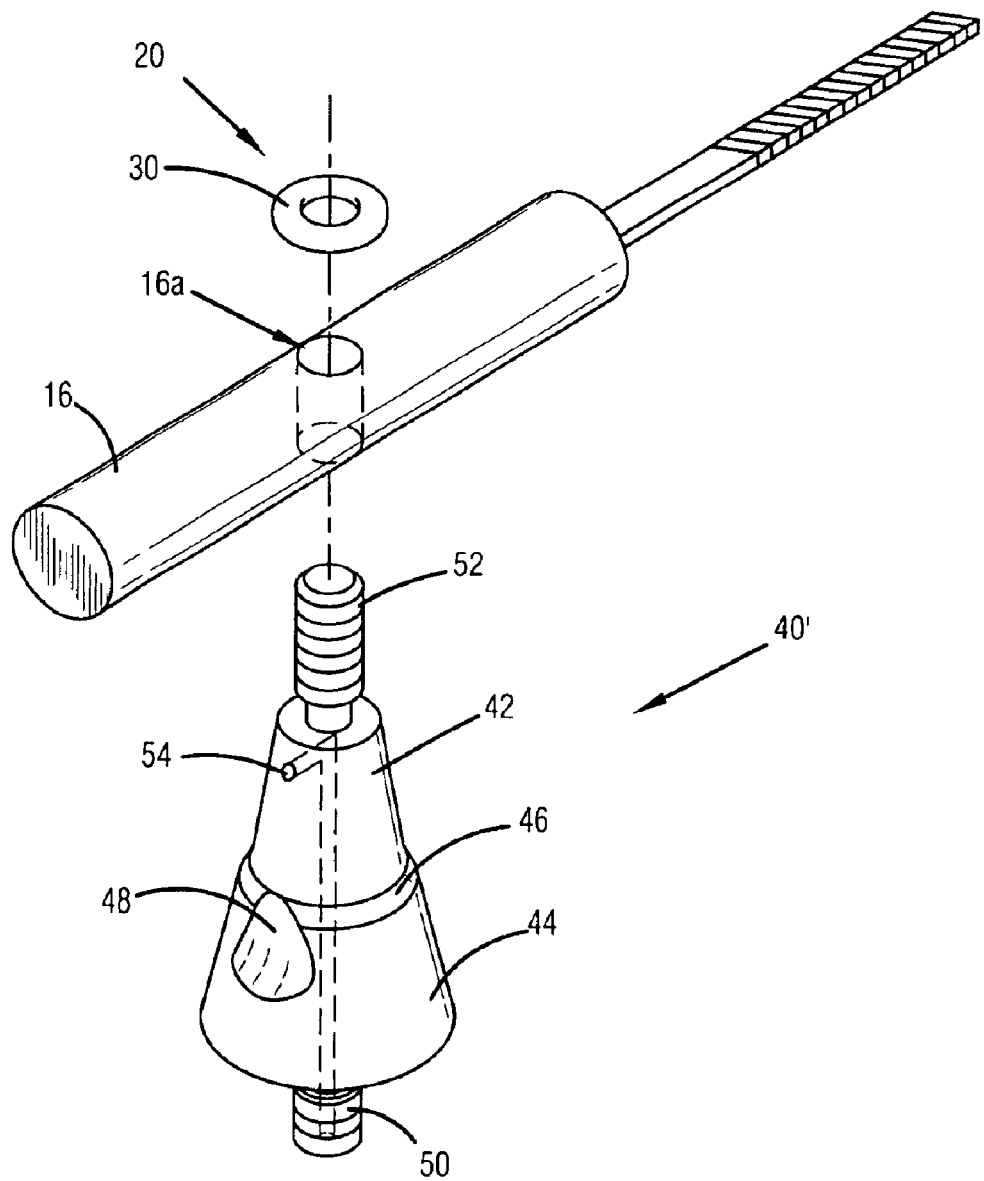
FIG. 9 is an exploded perspective view of the embodiment of the present invention shown in FIGS. 6–8; and, FIG. 10 is a perspective view of the embodiment of the present invention shown in FIG. 9.
Figure 10:
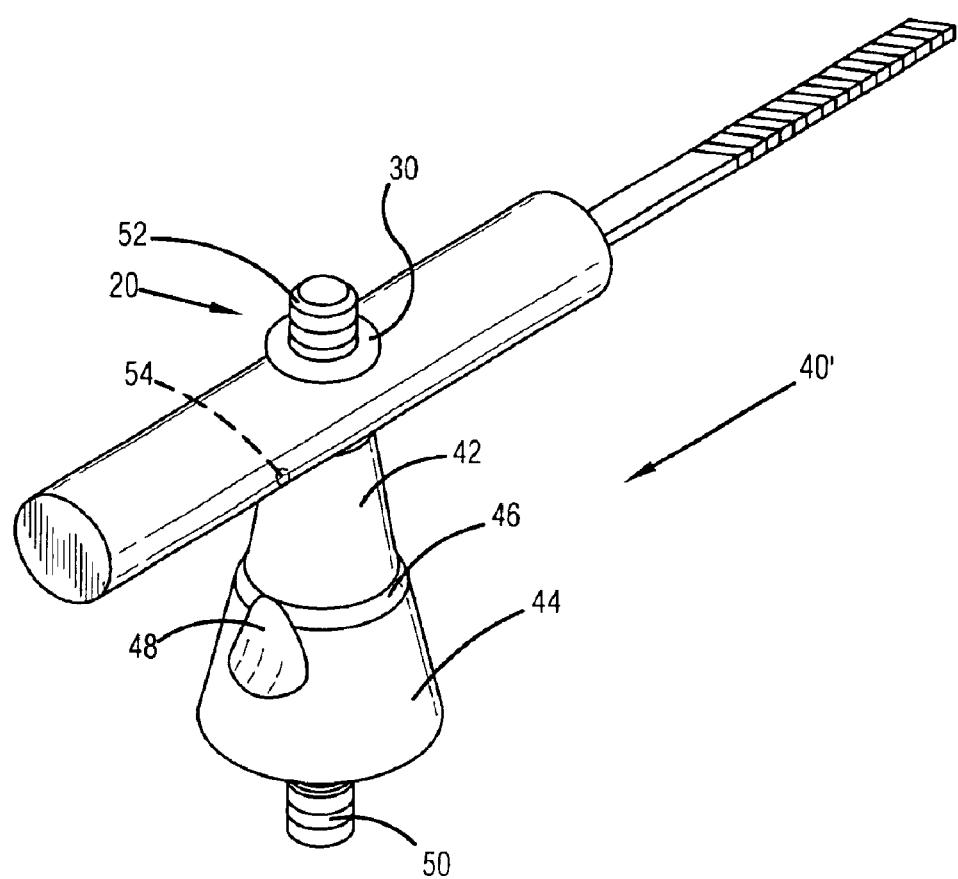

With specific reference to FIG. 9, the shaft 50 of the mounting head 40 is adapted to be inserted into the aperture 16a of the dental instrument 16. The aperture 16a is coincident with the transverse axis of the handle. The mounting head may be a single piece. The first conical 42 or frusto-conical section transitions into the second conical 44, or frusto-conical section through the shelf 46. The first frusto-conical section is laterally spaced from the second frusto-conical section. The first-frusto conical section has a first end with a diameter d1 and a second end with a diameter d2. The second frusto-conical section has a first end with a diameter d3 and a second end d4, wherein d1<d2<d3<d4.

The preferred embodiments have been described, hereinabove. It will be apparent to those skilled in the art that the above methods may incorporate changes and modifications without departing from the general scope of this invention. It is intended to include all such modifications and alterations in so far as they come within the scope of the appended claims or the equivalents thereof.

What is claimed is:

1. An apparatus, comprising:
    a medical instrument having a handle, said handle having a transverse axis, said handle having an aperture defined therein coincident with said transverse axis;
    a mounting head having a shaft extending therefrom, said shaft adapted to be inserted into the aperture defined in said handle of said medical instrument; and,
    a ligature operatively connected to said mounting head, said ligature adapted to secure said medical instrument to said mounting head, said ligature being at least partially elastic, said handle of said medical instrument being positioned between said elastic ligature and a first frusto-conical section;
    wherein said mounting head is a single piece and further comprises said first frusto-conical section transitioning into a second frusto-conical section via a shelf, said first frusto-conical section having a first end with a diameter $d1$ and a second end with a diameter $d2$, said second frusto-conical section having a first end with a diameter $d3$ and a second end $d4$, wherein $d1<d2<d3<d4$.

2. The apparatus of claim 1, wherein said mounting head is steel.

3. The apparatus of claim 1, wherein said mounting head is plastic.

4. The apparatus of claim 1, wherein said ligature is an o-ring.

5. A method for securing a medical instrument to a mounting head of a medical device, the method comprising the steps of:
    providing a medical instrument having a handle, said handle having a transverse axis, said handle having an aperture defined therein coincident with said transverse axis; and, said mounting head having a shaft extending therefrom, said shaft adapted to be inserted into the aperture defined in said handle of said medical instrument;
    inserting said shaft into the aperture of said medical instrument such that said medical instrument is substantially perpendicular to said mounting head; and
    securing said medical instrument to said mounting head with an elastic ligature, such that said medical instrument is positioned between the elastic ligature and a first frusto-conical section of said mounting head.

6. The method of claim 5, further comprising the step of:
    connecting said mounting head to a handle of said medical device.

7. The method of claim 5, wherein said elastic ligature is an o-ring.

8. An apparatus, comprising:
    a medical instrument having a handle, the handle having a transverse axis, said handle having an aperture defined therein coincident with said transverse axis; and,
    a mounting head having a shaft extending therefrom, said shaft adapted to be inserted into the aperture defined in said handle of said medical instrument, wherein said mounting head is a single piece and further comprises a first frusto-conical section transitioning into a second frusto-conical section via a shelf, said first frusto-conical section having a first end with a diameter $d1$ and a second end with a diameter $d2$, said second frusto-conical section having a first end with a diameter $d3$ and a second end $d4$, wherein $d1<d2<d3<d4$, wherein said shaft is threaded and extends from said first frusto-conical section.

9. The apparatus of claim 8, wherein said mounting head further comprises a threaded shaft extending from said second frusto-conical section for insertion into an associated handle of a sonic unit.

10. The apparatus of claim 8, further comprising an elastic ligature adapted to further secure said medical instrument to said shaft of said mounting head, so that said handle of said medical instrument is positioned between said elastic ligature and said first frusto-conical section.

11. The apparatus of claim 10, wherein said elastic ligature is an o-ring.

12. The apparatus of claim 10, wherein said elastic ligature is made from rubber.

13. The apparatus of claim 8, wherein said mounting head further comprises a water relief hole defined therein.

14. An apparatus, comprising:
    a mounting head having a shaft extending therefrom, said shaft adapted to be inserted into an aperture defined in an associated handle of a medical instrument, such that the medical instrument is substantially perpendicular to said mounting head, wherein said mounting head is a single piece and further comprises a first frusto-conical section transitioning into a second frusto-conical section via a shelf, such that said first frusto-conical section is laterally spaced from said second frusto-conical section, said first frusto-conical section having a first end with a diameter $d1$ and a second end with a diameter $d2$, said second frusto-conical section having a first end with a diameter $d3$ and a second end $d4$, wherein $d1<d2<d3<d4$, said shaft being threaded and extending from said first frusto-conical section.

* * * * *